United States Patent [19]

Johnson et al.

[11] 4,010,261

[45] Mar. 1, 1977

[54] METHOD TO PREVENT REPRODUCTION WITH [DES-GLY]$^{10}$-GN-RH NONADEPTIDE AMIDE ANALOGS IN POSITION

[75] Inventors: Edwin Samuel Johnson, Antioch; Riemond Henry Rippel, Jr., Gurnee, both of Ill.

[73] Assignee: Abbott Laboratories, North Chicago, Ill.

[22] Filed: Nov. 25, 1974

[21] Appl. No.: 526,482

[52] U.S. Cl. .................. 424/177; 260/112.5 LH
[51] Int. Cl.$^2$ ............... A61K 37/00; C07C 103/52
[58] Field of Search ................ 260/112.5; 424/177

[56] References Cited

UNITED STATES PATENTS 3,914,412   10/1975   Gendrick et al. ........ 260/112.5 LH

OTHER PUBLICATIONS

Schally et al.: Science, 179, 343–346 (1973).
Arimura et al.: Endocrinol., 80, 515–520 (1967).
Fujino et al.: Biochem. Biophys. Res. Comm., 57, 1248–1256 (1974).

Primary Examiner—Lewis Gotts
Assistant Examiner—Reginald J. Suyat
Attorney, Agent, or Firm—Paul D. Burgauer; Robert L. Niblack

[57] ABSTRACT

With the administration of 2 – 200 μg./kg. of a nonapeptide, reproduction is prevented in warm-blooded animals of the reproductive age.

6 Claims, No Drawings

METHOD TO PREVENT REPRODUCTION WITH [DES-GLY]¹⁰-GN-RH NONADEPTIDE AMIDE ANALOGS IN POSITION

DETAILED DESCRIPTION OF THE INVENTION

In the past few years, reproduction, conception and/or fertilization in warm-blooded animals has been prevented by the administration of a variety of physiologically active compositions, most of which consist of several components that occur naturally in said animals or synthetic analogs thereof. These components are, in some instances, given simultaneously and in others, are given separately at various times during a normal menstrual or ovulatory cycle. Unfortunately, some of these naturally present components or their synthetic analogs have other effects on the animals and exogenous administration thereof leads to undesirable side effects. For this reason, long-term use of such drugs is dangerous, and prevents widespread acceptance thereof.

It is therefore an object of this invention to prevent reproduction in female, warm-blooded animals in the reproductive age. It is a more specific object of this invention to provide a method to prevent reproduction of such animals by administration of an unnatural drug to said animals. It is an even more particular object of this invention to provide a method for preventing reproduction in mature female, warm-blooded animals by administration of a physiologically safe, synthetic chemical.

These and other objects are accomplished by providing a process for preventing reproduction by administering to a female, warm-blooded animal in or before reaching the reproductive age between 2 and 200 µg./kg./day of the nonapeptide L-pGlu-L-His-L-Trp-L-Ser-L-Tyr-X-L-Leu-L-Arg-L-Pro-NH-R wherein X denotes the optically active D-form off an aminoacid of the formula —NH—CHR'—CO— with R' being a linear or branched carbon chain of 1 - 4 carbon atoms and wherein R is loweralkyl, for at least one day in the period before said female produces one or more mature ova or after ovulation has occurred. The term "loweralkyl" is used to include alkyl groups containing between 1 and 7 carbon atoms. The divalent radical X may be best illustrated by the D-leucyl, D-alanyl, D-valyl or D-isoleucyl moieties.

The term "preventing reproduction" is intended to include preventing ova to form, including premature ovulation, preventing implantation of ova after fertilization postponing puberty or preventing embryo development. These various functions can be demonstrated in animal models; in turn, such experiments clearly show the general concept of preventing reproduction, be it by use of the nonapeptide in the follicular or luteal phase of the normal female reproductive cycle.

In a general embodiment, the above nonapeptide is administered to a cycling animal at a dose of 2 - 200 µg./kg./day as a single daily dose or divided into 2 - 4 daily doses of the equivalent smaller amounts. If this procedure is carried out during the time span where the ovum is expected to form, ovulation will not occur because ovum development is disrupted. If the nonapeptide is administered after fertilization has taken place, implantation does not occur and if the nonapeptide is given after implantation, the implanted ova will be expelled or the embryo will be resorbed.

In order to illustrate the process of the present invention, reference is made to the following examples which, however, are not to be construed as limiting the invention in any respect. In these examples and their discussion, the above-defined nonapeptide is referred to simply as "Compound N".

EXAMPLE 1

Female, immature rate (22 days old) are given 1.66 µg./day (2 × 0.83 µ6.) of Compound N (R' = isobutyl; R = ethyl) by subcutaneous injection of a 2% (wt./vol.) solution thereof in 0.1% aqueous bovine serum albumin and containing 0.9% sodium chloride. After 18 days, the ovarian weight of the sacrificed animals averaged 14.0 mg. with another group showing 22.8 mg. after 39 days of treatment. The corresponding control animals showed ovarian weights of 32.8 and 65.3 mg. after 18 or 39 days of treatment with saline alone. Also, after 39 days of treatment, the average uterine weight of the treated rats was found to be 69.9 whereas the control animals showed 276.5 mg.

This experiment shows that ovarian and uterine development can be postponed and animals can be kept in a prepubertal stage. However, no effect of Compound N remains after stopping its administration. This was demonstrated by finding that the animals exhibit estrus within 5 days of the last drug administration. Most of the animals successfully mated within 15 days and delivered normal litters.

EXAMPLE 2

Pregnant, adult rats weighing an average of 200 g. were used in this experiment. Ten animals were subcutaneously injected daily with 0.5 ml. b.i.d. with only the vehicle used in Example 2; ten animals received a solution of 1 µg. of Compound N (R' = isobutyl; R = ethyl) in 0.5 ml. b.i.d. dissolved at a concentration of 0.2% in the same vehicle and ten animals received 10 times this dose (concentration of 2%). In all instances, the subcutaneous injections were started on day 2 of gestation and continued daily b.i.d. until and including day 6. On day 15, the animals were sacrificed and the uteri were examined for the presence of viable implantations. The following table shows the results:

| Treatment | Number a) | Sites b) | % c) |
|---|---|---|---|
| 0.5 ml. Saline b.i.d. | 10/11 | 8.3 | 92% |
| 1 µg. Compound N | 1/10 | 10.0 | 0% |
| 10 µg. Compound N | 0/10 | 0 | 0% | a) number of animals with implants/number of animals treated
b) mean implantation sites (based on those with implantation sites)
c) viable fetuses/total number of fetuses (successful pregnancy)

This experiment demonstrates that Compound N inhibits successful implantation of the fertilized ovum.

EXAMPLE 3

In order to determine more clearly the results obtained in Example 2, three groups of pregnant rats were given subcutaneous doses of 10 µg./day b.i.d. on days 2 - 6, 3 - 6, and 4 - 6, inclusive of gestation. In the second group, only one rate in eight showed an implant but even in this instance, no viable fetus was noted in 4 implantation sites. The other two groups of 7 or 8 rats, respectively, showed no implant while in a control group of 8 animals, receiving 0.5 ml. of 0.1% bovine serum albumin b.i.d. subcutaneously on gestation days 2 – 6 inclusive, implantation was evident in 6 animals with an average of 11.5 nidation sites, of which 96% were viable.

EXAMPLE 4

Pregnant rabbits were given single subcutaneous injections of 50 μg./kg. of the compound used in Example 2 at various days of pregnancy. In a control group of 3 animals, a mean of 8 implants representing an average of 7 viable fetuses was observed (12% resorptions).

Upon injection on day 10 of gestation, an average of 7.6 implants, with 5 viable fetuses (34% resorptions) was observed in 5 pregnant does. The corresponding values with injections on day 14 were 7.4 implants, 1.2 viable fetuses (84% resorption) and with day 19 injections (3 animals), values of 7.7 implants, 1.7 viable fetuses (83% resorption) were found. In all instances, the animals were sacrificed at day 28 of pregnancy.

EXAMPLE 5

Pregnant rabbits were given subcutaneous, single injections of 50 μg. of the compound used in Example 1 on day 20 of pregnancy. In a control group of 5 animals, 100% viable embryos were found upon sacrifice on day 29 of pregnancy; in the group of 5 animals treated with Compound N, there are 40% viable embryos.

In a separate test, 10 pregnant rabbits were randomly divided into two equal groups, one being used as control group, the other being treated as above on day 14 of pregnancy. This group showed a total of 13% viable embryos while the control group showed 100% upon sacrifice on day 22 of pregnancy.

EXAMPLE 6

In order to determine more precisely the fate of the implanted ovum in rats, a 2% solution of Compound N (R'= isobutyl; R = ethyl) in water containing 0.1% bovine serum albumin and 0.9% sodium chloride was injected subcutaneously into rats at various days gestation. In each instance, two doses of 1 or 10 μg. of Compound N was given per day on the days indicated.

No viable fetuses were observed in 2 groups of 10 animals each upon treatment with 1 and/or 10 μg. on days 2 – 6 inclusive. With 10 μg. on days 4 – 6 inclusive, no viable fetuses were obtained in 7 animals; the same dose given to 7 animals (per group), at days 4 and 5, on days 5 and 6, on day 4 only and on day 5 only showed implants in 2, 5, 7 and 7 animals, respectively with 94%, 66%, 90% and 86% viable fetuses, respectively.

Since implantation is known to take place 5 or 5½ days after mating, the above 10 μg. regimen was administered on days 6 and 7, only on day 6 and only on day 7 with 8 animals per group. Implants were found in 2, 5, and 6 animals respectively with 15% 92% and 62% viable fetuses, respectively.

EXAMPLES 7 – 10

In this experiment, the activity of various compounds encompassed under Compound N are desmonstrated. Groups of 8 – 10 pregnant rats were injected subcutaneously b.i.d. with 0.5 ml. of the medium shown in Example 1 containing the compound and dose identified below. The results are expressed as explained in Example 2.

| Example | R' | R | Dose | a | b | c |
|---|---|---|---|---|---|---|
| 7 | iBu | Et | 10 μg. | 0/10 | 0 | 0% |
| 8 | Me | Et | 10 μg. | 0/10 | 0 | 0% |
| 9 | iBu | Bu | 25 μg. | 5/10 | 10 | 40% |
| 10 | iBu | Me | 25 μg. | 0/10 | 0 | 0% |
| Control | — | — | — | 9/10 | 9.6 | 92% |

As shown above, the treatment with Compound N in small amounts at almost any time during the female cycle has a profound effect on fertility or reproduction. In most instances, single doses of 2 – 200 μg./kg. of body weight are sufficient but it may be desirable to administer the above nonapeptide daily for several days depending on the length of cycle of the particular animal involved.

In the case of humans, oral administration is preferred for reasons of simplicity. Daily doses of 2 – 50 μg. kg. for several days following menses or after ovulation will prevent pregnancy. Tablets containing 100 – 500 μg. represent a particularly suitable dosage unit range. Tablets of this type are prepared in the usual fashion by compounding the active ingredient with starch, granulating the mixture and, after adding the necessary fillers, flavoring agents, lubricants, etc., the mixture is slugged and passed through a 30-mesh screen. The thoroughly blended mixture is then compressed into the tablets of desired hardness with the usual punch, preferably to make bisected tablets for easier b.i.d. administration.

In animals, subcutaneous administration may be more desirable. In this instance, the active ingredient is dissolved in physiologically acceptable saline optionally containing 0.05 – 1% by weight of serum albumin at a concentration of between 0.5 and 10% by weight of Compound N for injection in order to prevent pregnancies or, if desired, to synchronize a herd for flock of animals.

The demonstrated effects on the animals' reproductive cycle by the compounds of this invention are primarily based on the imbalance of steroid hormones caused therewith in the reproductive organs of the animals treated. This can be demonstrated by administering to the Compound N-treated-animals exogenous estrogens. More specifically, if estradiol is subcutaneously given to rats treated with Compound N (days 2 – 6 of gestation) on days 4 and 5 of gestation at a dose of as little as 0.1 μg. each (dissolved in sesame oil), implantation already takes place in 3 of 8 animals, producing 100% viable embryos. The process of this invention can therefore be summarized as being a process of preventing the proper balance of steroids in the reproductive organs, thereby causing the demonstrated inability to reproduce.

The process of the current invention thus can be used to prevent ovulation in immature animals in order to postpone their entering the reproductive cycle; it can be used to delay the maturation of ova and thus synchronize a heard, flock drove, pack or other aggregations of animals; it can be used after ovulation to prevent implantation. In either case, reproduction is prevented. The new process can also be used to prevent fertilization by inducing premature ovulation and can be used to inhibit implantation of the ova before it is attached to the uterus or thereafter to cause abortive action in the embryo.

What is claimed is:

1. The process for preventing reproduction consisting essentially in administering to a female, warm-blooded animal in or before reaching the reproductive age, between 2 – 200 µg./kg./day of the nonapeptide L-pGlu-L-His-L-Trp-L-Ser-L-Tyr-X-L-Leu-L-Arg-L-Pro-NH-R wherein X denotes the optically active D-form of an aminoacid of the formula —NH—CHR'—CO— with R' being a linear or branched carbon chain of 1 – 4 carbon atoms and wherein R is loweralkyl for at least one day in the period before said female produces one or more mature ova or after ovulation has occurred.

2. The process of claim 1 wherein X in said nonapeptide is D-leucyl and R is ethyl.

3. The process of claim 1 wherein X is D-alanyl and R is ethyl.

4. The process of claim 1 wherein X is D-leucyl and R is propyl.

5. The process of claim 1 wherein said nonapeptide is given as a single dose of between 2 and 200 ug./kg.

6. The process of claim 5 wherein said dose is administered orally.

* * * * *